(12) United States Patent
Unver et al.

(10) Patent No.: US 10,874,545 B2
(45) Date of Patent: Dec. 29, 2020

(54) HEAT EXCHANGER

(71) Applicant: Paxman Coolers Limited, Huddersfield (GB)

(72) Inventors: Ertugrul Unver, Bradford (GB); Glenn Alan Paxman, Holmfirth (GB); Neil Eric Paxman, Holmfirth (GB)

(73) Assignee: PAXMAN COOLERS LIMITED, Huddersfield (GB)

( * ) Notice: Subject to any disclaimer, the term of this patent is extended or adjusted under 35 U.S.C. 154(b) by 193 days.

(21) Appl. No.: 15/512,707

(22) PCT Filed: Sep. 22, 2015

(86) PCT No.: PCT/GB2015/052739
§ 371 (c)(1),
(2) Date: Mar. 20, 2017

(87) PCT Pub. No.: WO2016/046534
PCT Pub. Date: Mar. 31, 2016

(65) Prior Publication Data
US 2017/0239082 A1 Aug. 24, 2017

(30) Foreign Application Priority Data

Sep. 23, 2014 (GB) .................................. 1416765.4

(51) Int. Cl.
*A61F 7/02* (2006.01)
*A61F 7/00* (2006.01)

(52) U.S. Cl.
CPC ........ *A61F 7/02* (2013.01); *A61F 2007/0008* (2013.01); *A61F 2007/0054* (2013.01);
(Continued)

(58) Field of Classification Search
CPC ................ A61F 7/02; A61F 2007/0002; A61F 2007/0008; A61F 2007/0054;
(Continued)

(56) References Cited

U.S. PATENT DOCUMENTS 1,404,320 A 1/1922 Roberts et al.
1,896,953 A 2/1933 Hassell
(Continued)

FOREIGN PATENT DOCUMENTS

CN 2406636 Y 11/2000
DE 1454922 A1 4/1969
(Continued)

*Primary Examiner* — Michael F Peffley
*Assistant Examiner* — Bo Ouyang
(74) *Attorney, Agent, or Firm* — Coats & Bennett, PLLC

(57) ABSTRACT

A heat exchanger, and method of manufacture of a heat exchanger configured to be placed into contact with an object to regulate the temperature of the object. The heat exchanger comprises a layer of material defining a passage through which a heat transfer fluid may flow. The material layer has a first side for contact with the object; and a second side which, in use, will face away from the object. The first side has a relatively high coefficient of thermal conduction. The second side has a relatively low coefficient of thermal conduction compared to the first side.

12 Claims, 8 Drawing Sheets

(52) U.S. Cl.
CPC ............. *A61F 2007/0098* (2013.01); *A61F 2007/0233* (2013.01); *A61F 2007/0247* (2013.01); *A61F 2007/0249* (2013.01); *A61F 2007/0253* (2013.01)

(58) Field of Classification Search
CPC ..... A61F 2007/0056; A61F 2007/0098; B29C 51/10; B29C 51/105
See application file for complete search history.

(56) References Cited

U.S. PATENT DOCUMENTS

| | | | |
|---|---|---|---|
| 2,726,658 A | | 12/1955 | Chessey |
| 3,242,245 A | * | 3/1966 | Cunningham ...... B29C 49/0047 156/285 |
| 3,256,565 A | | 6/1966 | Alesi et al. |
| 3,867,939 A | | 2/1975 | Moore et al. |
| 4,566,455 A | | 1/1986 | Kramer |
| 4,987,896 A | | 1/1991 | Nakamatsu |
| 5,086,771 A | | 2/1992 | Molloy |
| 5,169,384 A | | 12/1992 | Bosniak et al. |
| 5,342,411 A | | 8/1994 | Maxted et al. |
| 5,469,579 A | | 11/1995 | Tremblay et al. |
| 5,603,728 A | | 2/1997 | Pachys |
| 5,630,230 A | | 5/1997 | Fujino et al. |
| 5,802,865 A | | 9/1998 | Strauss |
| 5,895,418 A | | 4/1999 | Saringer |
| 5,950,234 A | | 9/1999 | Leong et al. |
| 6,117,164 A | | 9/2000 | Gildersleeve et al. |
| 6,156,059 A | | 12/2000 | Olofsson |
| 6,178,562 B1 | | 1/2001 | Elkins |
| 6,312,453 B1 | * | 11/2001 | Stefanile ............... A61F 7/10 607/108 |
| 6,375,674 B1 | | 4/2002 | Carson |
| 6,427,467 B1 | | 8/2002 | Bell |
| 6,681,590 B1 | | 1/2004 | Jones |
| 7,721,349 B1 | | 5/2010 | Strauss |
| 2002/0058976 A1 | | 5/2002 | Lee |
| 2002/0091431 A1 | * | 7/2002 | Gunn ................. A61F 7/02 607/110 |
| 2003/0088299 A1 | | 5/2003 | Magers et al. |
| 2005/0028551 A1 | | 2/2005 | Noda et al. |
| 2005/0107855 A1 | | 5/2005 | Lennox et al. |
| 2005/0132468 A1 | | 6/2005 | Lundgren |
| 2005/0187502 A1 | | 8/2005 | Krempel et al. |
| 2006/0235496 A1 | | 10/2006 | Collins et al. |
| 2008/0184456 A1 | | 8/2008 | Fontanez |
| 2008/0228248 A1 | | 9/2008 | Guyuron et al. |
| 2008/0269852 A1 | | 10/2008 | Lennox et al. |
| 2009/0054958 A1 | | 2/2009 | Nofzinger |
| 2010/0030306 A1 | | 2/2010 | Edelman et al. |
| 2010/0095641 A1 | * | 4/2010 | Ruetenik ............ A01K 13/007 54/82 |
| 2010/0186436 A1 | | 7/2010 | Stormby |
| 2010/0319110 A1 | | 12/2010 | Preston-Powers |
| 2012/0283534 A1 | * | 11/2012 | Carr .................. A61B 5/01 600/324 |
| 2013/0138185 A1 | * | 5/2013 | Paxman ............. A61F 7/0085 607/104 |
| 2013/0226044 A1 | | 8/2013 | Moore et al. |
| 2014/0046410 A1 | | 2/2014 | Wyatt |
| 2014/0172050 A1 | | 6/2014 | Dabrowiak |
| 2014/0222121 A1 | | 8/2014 | Spence et al. |
| 2014/0276253 A1 | * | 9/2014 | Varga .................. A61F 7/02 601/15 |
| 2014/0277302 A1 | | 9/2014 | Weber et al. |

FOREIGN PATENT DOCUMENTS

| | | |
|---|---|---|
| DE | 102011100616 A1 | 11/2011 |
| EP | 1520568 A1 | 4/2005 |
| GB | 2323915 A | 10/1998 |
| GB | 2482792 A | 2/2012 |
| JP | 05278081 A | 10/1993 |
| JP | 2002316357 A | 10/2002 |
| KR | 20070088224 A | 8/2007 |
| WO | 0003666 A1 | 1/2000 |
| WO | 0038601 A1 | 7/2000 |
| WO | 0162193 A2 | 8/2001 |
| WO | 0200132 A1 | 1/2002 |
| WO | 2006110405 A2 | 10/2006 |
| WO | 2013074128 A2 | 5/2013 |
| WO | 2013190333 A2 | 12/2013 |

* cited by examiner

HEAT EXCHANGER

The present disclosure relates to a heat exchanger.

In particular the disclosure is concerned with a heat exchanger configured to be placed into contact with an object to regulate the temperature of the object.

BACKGROUND

Various medical treatments involve the cooling of a body part. In the treatment of cancer, it is known to cool the head of a patient during chemotherapy in order to reduce the extent and/or likelihood of hair loss.

Shown in FIG. 1 is an example of a known cooling cap 10. The cooling cap 10 comprises a single tube 12 in a concentric hoop arrangement, stacked on top of itself, to form a part spherical garment to be worn on a patient's head. The tube 12 has a fluid inlet 14 and a fluid outlet 16. In use, coolant is pumped from the inlet 14 to the outlet 16 to thereby remove heat from a contact area with the patient.

The cap 10 is formed by wrapping the tube 12 around the outside of a dome shaped former and gluing sides of the tube 12 to one another, which is time consuming. Additionally, as the cap 10 is for contact with a human body part, the cap materials, including adhesive, must conform to medical regulatory standards, which limits the range of adhesives available, and also increases the cost of manufacture.

FIG. 2 shows a cross section of cap 10, with the tube 12 in contact with a head 20 of a patient. As shown in FIG. 2, an over wrap layer 18 may be provided as part of the cap 10, on the outer surface of the tubes 12. In the arrangement in FIG. 2, it can be seen that while the tube 12 makes contact with the head 20, there is a large gap 22 between the contact regions where the tubes 12 do not touch the head 20. Even when the over layer 18 is drawn in to bring the tubes 12 tightly against the subject's head 20, as shown in FIG. 3, gaps 22 still remain where the tubes 20 do not make contact with the subject's head.

Hence, while the principle of construction and operation of cap 10 is sound, it results in a cap which is problematic and time consuming to manufacture, and a device which leaves significant gaps 22 between tubes 12, and hence where tubes are not in contact with the subjects head when the cap is worn. Hence not all of the area of the head are cooled to the same extent. This may limit the effectiveness of the treatment given by such a cap 10.

Hence a heat exchanger which is easier, and therefore quicker, to manufacture and which provides a more even cooling effect on the object to which it is applied is highly desirable.

SUMMARY

According to the present invention there is provided apparatus, system and a method as set forth in the appended claims. Other features of the invention will be apparent from the dependent claims, and the description which follows.

Accordingly there may be provided a heat exchanger configured to be placed into contact with an object to regulate the temperature of the object, the heat exchanger comprising a layer of material defining a passage through which a heat transfer fluid may flow; the material layer having: a first side for contact with the object; and a second side which, in use, will face away from the object; wherein the first side has a relatively high coefficient of thermal conduction; and the second side has a relatively low coefficient of thermal conduction compared to the first side.

The first side may be relatively flexible and configured to be compliant and to conform to the shape of the surface of the object; and the second side is relatively inflexible compared to the first side.

The first side may comprise a relatively thin silicone based wall; and the second side comprises a relatively thick silicone based wall compared to the first side.

The wall of the first side may comprise aluminium particles.

The second side may comprise an insulatory layer outward of the silicone wall.

At least part of the first side may have, in a non deformed state, a double arced outer surface, with both arcs configured for contact with the object.

At least part of the second side may have, in a non deformed state, a single arcuate outer surface.

The passageway may have a boustrophedonic route throughout the majority of the layer, the passageway extending from a single inlet to a single outlet.

The boustrophedonic route of the passageway in each element may be from the nominal front of the heat exchanger to the nominal back of the heat exchanger.

The layer may be divided into regions, the passageway in at least one region having a boustrophedonic route.

The object may be a human or animal body part.

There may be provided a garment comprising a heat exchanger according to the present disclosure.

There may be provided a cap to be worn on a human or animal head a heat exchanger according to the present disclosure.

There may also be provided a method of manufacture of a heat exchanger according to the present disclosure, the method comprising: providing a first former having a surface pattern which defines the external shape of one side of the layer; providing a second former having a surface pattern which defines the external shape of the other side of the layer, the patterns of both formers being complementary in shape to thereby define the route of the passageway in the layer; sandwiching a sheet of the first material next to a sheet of the second material such that the first sheet separates the first former from the second sheet, and the second sheet separated the second former from the first sheet; and executing a joining process including bringing the two formers together such that the first material sheet and second material sheet are brought into contact to undergo a joining process.

The joining process may comprise bringing the layers together at ambient temperature conditions.

The first sheet material and second sheet material may comprise a silicone rubber.

The method further may further comprise the step of, when the formers are together, at least partially evacuating the internal passageways of the former thereby force the first and second sheet materials towards the walls of the formers, thereby deforming the sheet materials to the shape of the former to thereby provide the sheet with a desired external cross sectional shape.

The former may define the shape of at least part of a cap to conform to a human or animal head, or of sections of a cap to be joined to other sections to make a cap.

There is thus provided a heat exchanger with an improved heat transfer performance. The heat exchanger may take the form of a garment or cap. There is also provided a method of manufacture of a heat exchanger which provides a more repeatable, consistent and faster method of manufacture than that known in the art.

BRIEF DESCRIPTION OF THE DRAWINGS

Examples of the present disclosure will now be described with reference to the accompanying drawings, in which.

DETAILED DESCRIPTION

Figure 4:
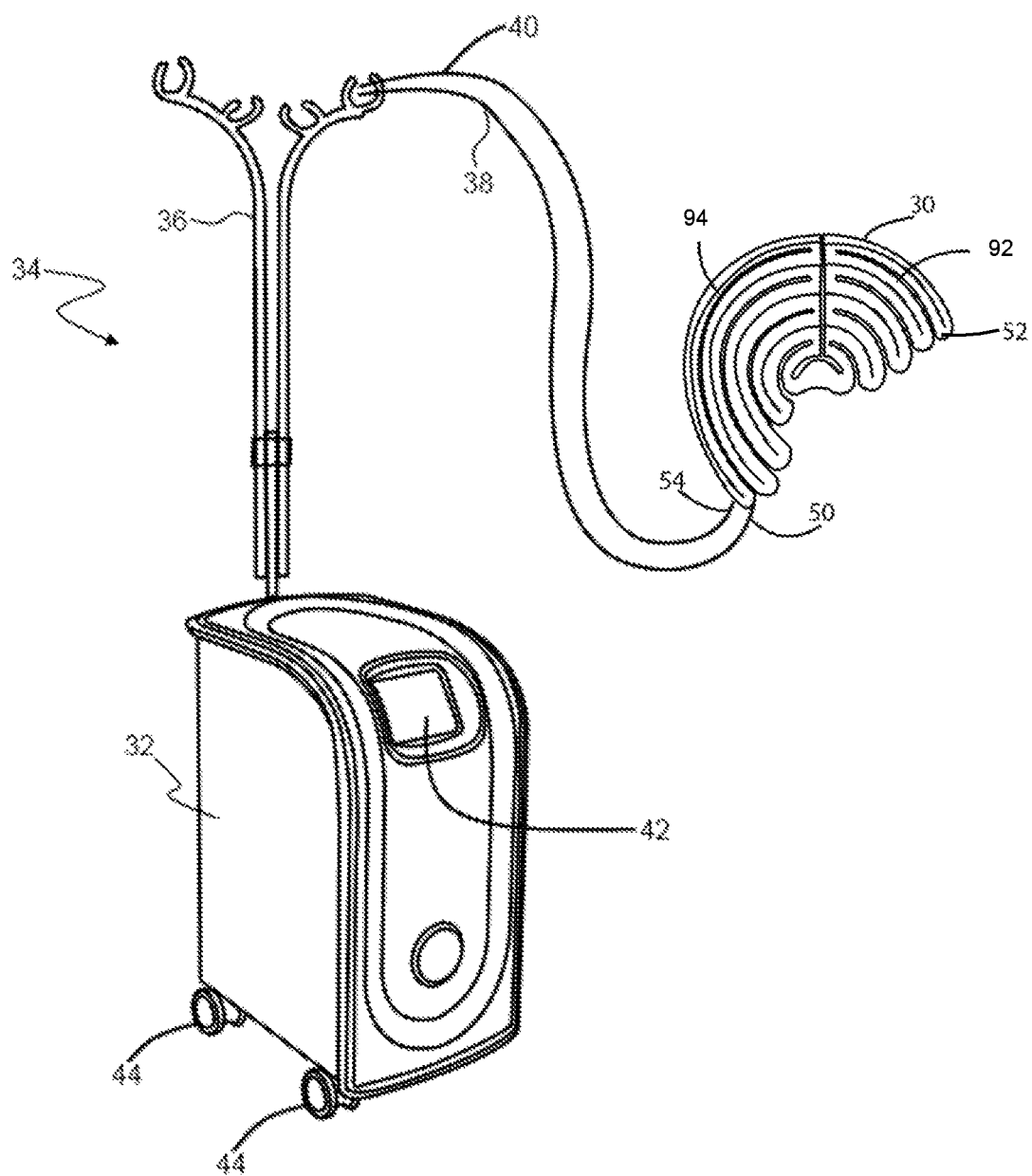
FIG. 4 shows temperature regulation system according to the present disclosure, including a heat exchanger according to the present disclosure.

FIG. 4 shows an example of a heat exchanger 30 in combination with a fluid flow and temperature control unit 32 (or system) to form a fluid temperature control regulation system 34 for regulating the temperature of an object. The object may be a human or animal body part. The heat exchanger may form part of a garment. For example, the heat exchanger may form part of a cap to be worn on a human or animal head.

In the example shown, the heat exchanger is provided in the form of a cap for wearing on a human head. A stand frame 36 for the support of fluid supply and return tubes 38, 40 extends from the control unit 32. The tube 38 delivers temperature regulation fluid (that is to say, a heat transfer fluid) to the cap 30. The tube 40 receives the same temperature regulation fluid from the cap 30. The control unit 32 is controllable by a user via an interface panel 42, which may also present information relevant to the operation of the system 34. The control unit 32 is provided with rollers 44 such that it is easily transportable.

In operation, a user operates the system 34 to regulate a patient's head temperature to a desired valve. In particular, the system is configured for cooling a patient, and in such examples the temperature regulation fluid will be a coolant. In other examples the system 34 may be configured to heat or maintain the body temperature of the patient. Regulation of the fluid flow rate, and temperature of the temperature regulation fluid to achieve a desired heat transfer rate, thereby bringing the patient's temperature to the desired level, are controlled in dependence upon the users input requirements. The fluid is pumped via the delivery tube 38 to an inlet 50 to the cap 30. The fluid then passes through a single passageway 52 provided in the cap 30, and exits the cap 30 at an outlet 54 (hidden from view in FIG. 4) to enter the return tube 40, and hence re-enter the system 34 to be brought back to the required temperature.

The shape, form and constituent elements of the cap, and method of manufacture of the cap will be now be described with reference to FIGS. 5 to 15.

Figure 5:
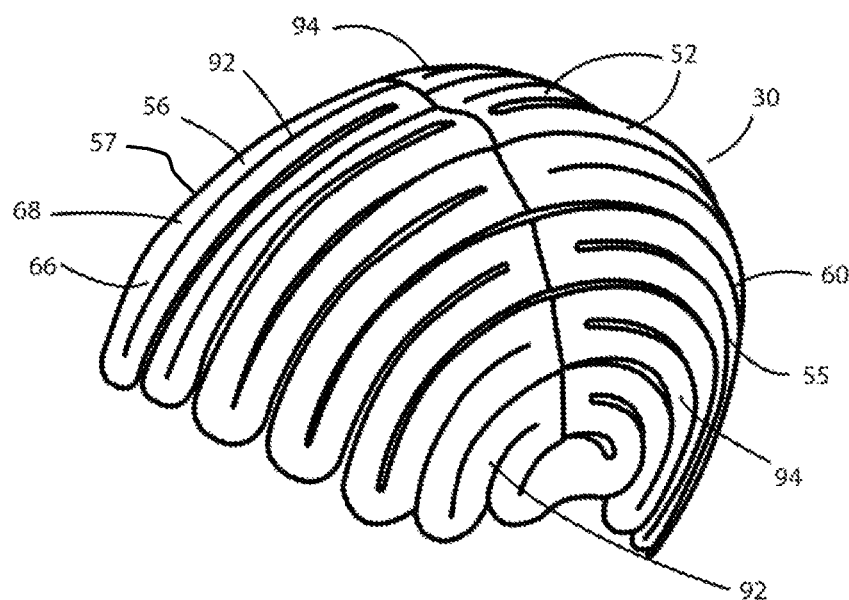
FIG. 5 shows a perspective view of part of the heat exchanger of the present disclosure.
Figure 6:
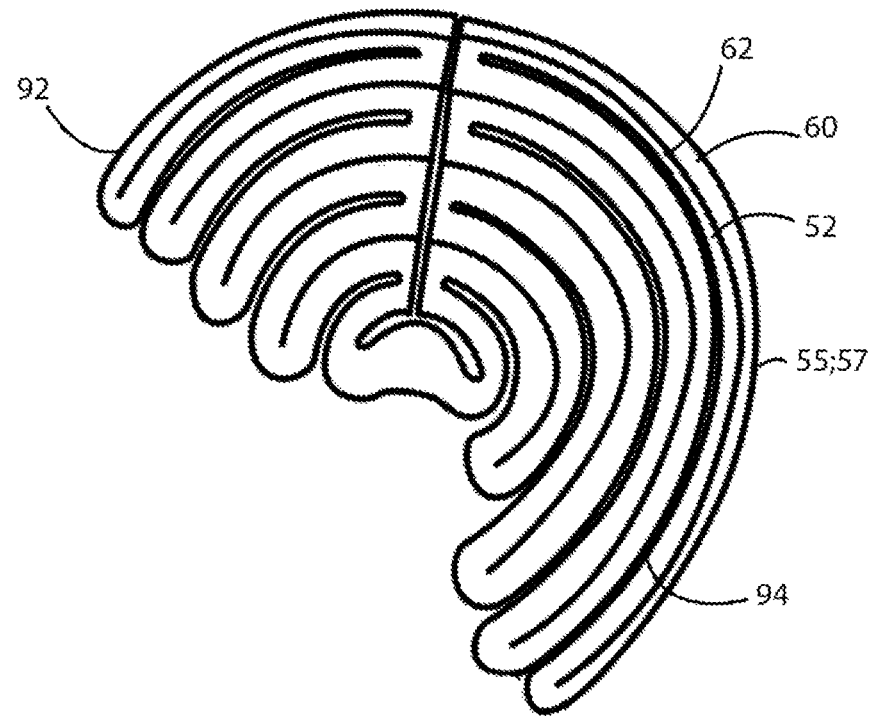
FIG. 6 shows an enlarged view of the underside of a region of the heat exchanger as shown in FIG. 5.

FIG. 5 shows a perspective view of the external side of the heat exchanger 30 of the present disclosure, fitted to a human head. It will be appreciated that the view shown is of a feature of the cap, and is not necessarily representative on what the cap will look like in practice. FIG. 6 shows an enlarged view of the inner side of the heat exchanger 60, namely the side which contacts the object to be cooled.

The cap 30 comprises a first element 55 for covering one side of the head, a second element 56 for covering the other side of the head, and an intermediate joining element 57 which covers the tope of the head. Each of the elements 55, 56, 57 define a section of the single passageway 52 through the cap 30 for the passage of the temperature regulation fluid.

Each element may be provided as combination of joined layer materials, spaced apart in regions which define the passageways 52, and joined in other regions between the adjacent sections of passageway 52. However, the elements may be manufactured by any appropriate method, being made from any number of parts or formed integrally as one piece, to form a heat transfer layer 60. In other examples, the heat exchanger 30 may be provided as a layer 60 having unified construction.

However, common to all examples is a heat transfer layer 60 comprising the single passageway 52. The layer 60 comprises sheets of material which define the passage 52 through which a heat transfer fluid (i.e. a coolant) may flow.

The layer 60 has a single inlet 50 and a single outlet 54, as indicated in FIG. 4. The inlet and outlet may comprise a number of apertures and sub-structures. However, there is provided only one entrance (inlet) region to the passageway of the cap, regardless of how or where that inlet may be provided and/or configured. Likewise there is provided only one outlet region from the cap, however or wherever that outlet may be provided or configured.

In the examples shown in FIGS. 4 to 6, the route of the passageway 52 is defined by the walls of the material layer 60 such that the passageway 52 has a boustrophedonic or serpentine route throughout the majority of the layer 60. The passageway 52 extends from the single inlet into the heat exchanger to the single outlet from the heat exchanger.

The layer 60 may be divided into regions, the passageway in at least one region having a boustrophedonic route.

In at least one region of the cap, the passageway 52 has a boustrophedonic route between the cap inlet 50 and cap outlet 54.

The boustrophedonic route of the passageway 52 is back and forth aligned with a direction from the nominal front of the cap 30 towards the nominal back of the cap 30. That is to say, as shown in FIGS. 5, 6, the passageway has a serpentine route having a turning point at the nominal front of the cap which corresponds to the front of the head upon which it sits, and a turning point along a line aligned with the direction between the front and back of the head at a point between the front and back of the head.

Additionally, and as shown in the figures, the passageway 52 has a boustrophedonic, or serpentine, route in each of the elements 55, 56, 57, the boustrophedonic route being provided from the nominal front of the cap to the nominal back of the cap, with a turning point at approximately halfway between the front and back of the cap which abuts another turning point which is the leading end of another backwards and forwards run of the passageway. One or more of the elements 55, 56, 57 may be divided into flow regions. For example, with reference to the first immediate element, or second element 55, 56, 57 shown in FIG. 5 and FIG. 6, there may be provided a first flow region 92 and a second flow region 94 where the passageway 52 is arranged to have a local pattern to correspond to a pre-determined part of the head. In the example shown in FIGS. 5, 6, the local pattern is defined by the forward and backward route of the passageway 52 over substantial nominal front half of the side of the cap, which corresponds to the nominal front half of the side of the head on which it will be worn. The second region 94 defines a backwards and forwards serpentine passageway route which covers the nominal back half of the side of the cap 30, and hence the nominal back half of the head on which the cap 30 will worn. Put another way, the flow regions 92,94 may define a volume of the cap 30 in which the passageway 52 extends only part of the way, and not the whole of the way, from the front to the back of the cap 30. Likewise the intermediate element 55 may comprise region where the route of the passageway from back to front of the element is truncated.

Regional variations in the patterns of passageway 52 (such as the regions 92, 94) may be provided to focus temperature regulation (for example, cooling) in particular locations on a human head which commonly have specific temperature characteristics. For example, where regions of the human head are known to be generally warmer than other regions, then the passageway 52 may be provided in those regions to provide a different heat transfer rate between the cap and the head. For example, there will be a region of different heat transfer rate (compared to the other regions of the passageway 52) along the line of the junction between the regions 92,94 as shown in FIG. 5.

In the examples shown, the passageway 52 has a substantially constant cross-sectional area along its length, from inlet 50 to outlet 54. Additionally, the passageway 52 has a substantially constant cross-sectional shape along its length, from inlet 50 to outlet 54.

In other examples, the cross-sectional area of the passageway 52 may vary in size and shape along its length.

Figure 7:
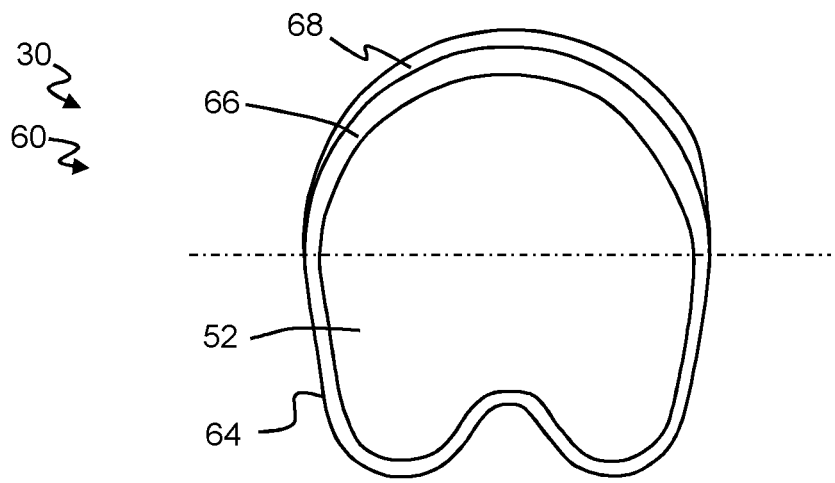
FIG. 7 shows a cross-section of a region of the heat exchanger as shown in FIGS. 5 and 6.

A cross-section of the layer 60 showing the walls of the material layer 60 which define the passage 62 is shown in FIG. 7. The material layer 60 has a first side 64 for contact with the object, and a second side 66 which in use will face away from the object. The first side 64 is configured to have a relatively high co-efficient of thermal conduction relative to the second side 66, which is configured to have a relatively low co-efficient of thermal conduction. Additionally, the first side 64 is configured to be relatively flexible and configured to be compliant and to conform to the shape of the surface of the object to which it will come into contact, in use. The second side 66 is relatively inflexible, and hard, compared to the first side 64. The wall of the first side 64 comprises a relatively thin silicone based material. The wall of the first side 64 may comprise particles of aluminium held in the wall, the silicone wall acting as a substrate. The particles of aluminium increase the thermal conductivity of the silicone substrate in which they are held.

The wall of the second side 66 is relatively thick compared to the wall of the first side 64. The wall of the second side 64 may also comprise silicone. The composition of the material of the second side 66 may be different to the composition of the material on the first side 64. The second side 66 may also comprise an additional insulatory layer 68, which may be outward of the silicone wall defining the second side 66. Alternatively, the insulator layer may be inward of the silicone wall, or partly or completely embedded in the wall of the second side 66.

The first side 64, in a non-deformed state, comprises an undulating outer surface. For example, the first side 64, which in use will contact the object to be temperature regulated, has a double arced outer surface, with both arcs configured for contact with the object. That is to say, the first side 64 has a surface with a three points of inflection such that it is a rounded "w" shape, or "$\omega$" shaped. Some regions of the first side may also comprise a different profile, for example a flattened profile.

The second side 66 has, in a non-deformed state, a single arced outer surface. That is to say the second side 66 in a non-deformed state, is substantially semi-circular in cross-section. Some regions of the first side may additionally, or alternatively, comprise a different profile, for example a flattened profile.

Figure 8:
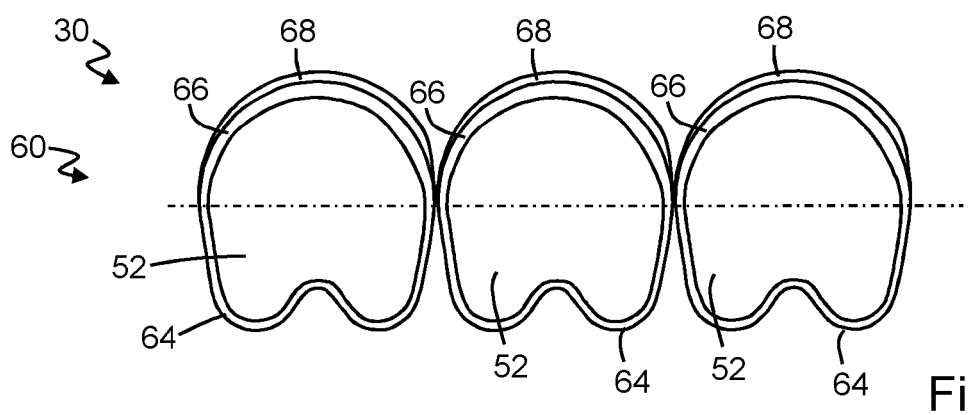
FIG. 8 shows a further cross-section of a heat exchanger according to the present disclosure.

FIG. 8 shows a cross-section of a region of the cap 30, which shows three adjacent runs of the passageway 52 next to one another. FIG. 8 illustrates the profile of the first side 64 of the wall of the material layer 60 defining the passageway 52 and the second side 66 of the material layer 60 when the layer 60 is not in contact, or only lightly in contact, with an object. Hence FIG. 8, the layer is shown in a non-deformed state, with the undulating nature of the first side evident.

Figure 1:
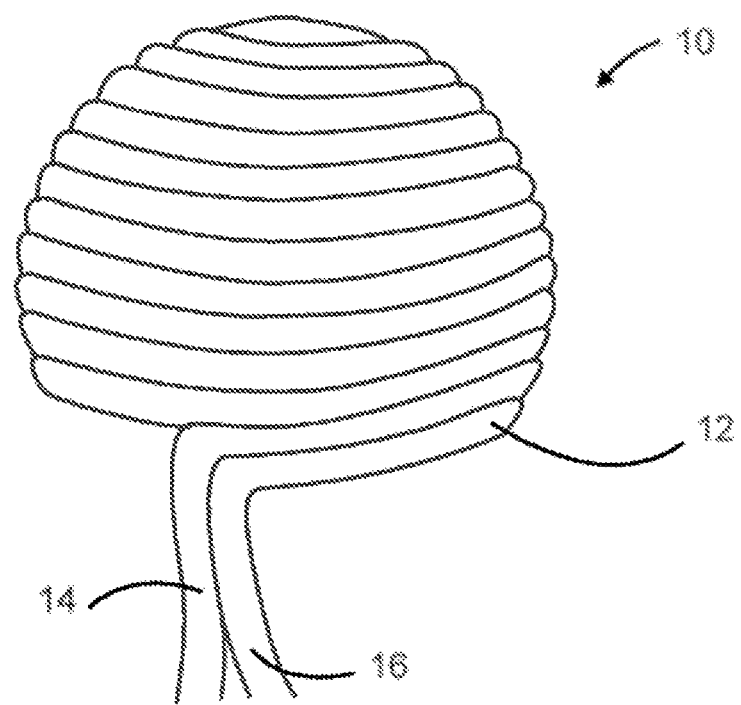
FIGS. 1 to 3 show an example cooling cap of the related art.
Figure 2:
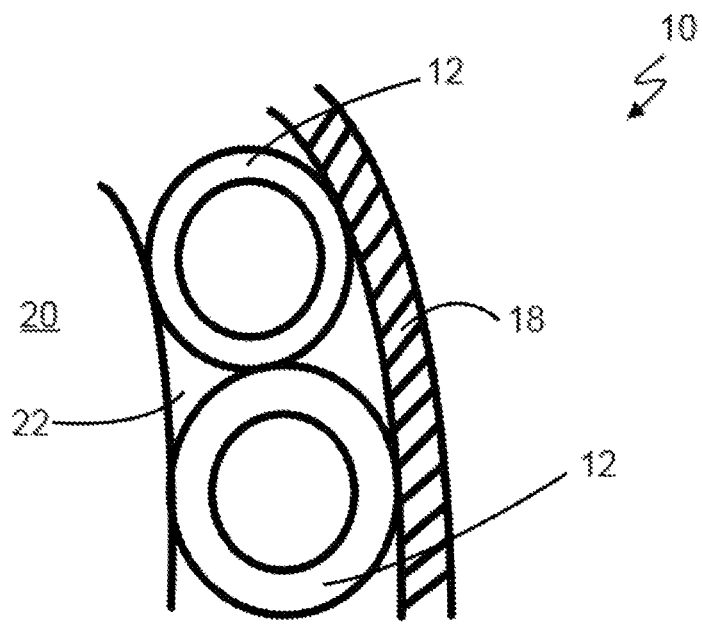
Figure 3:
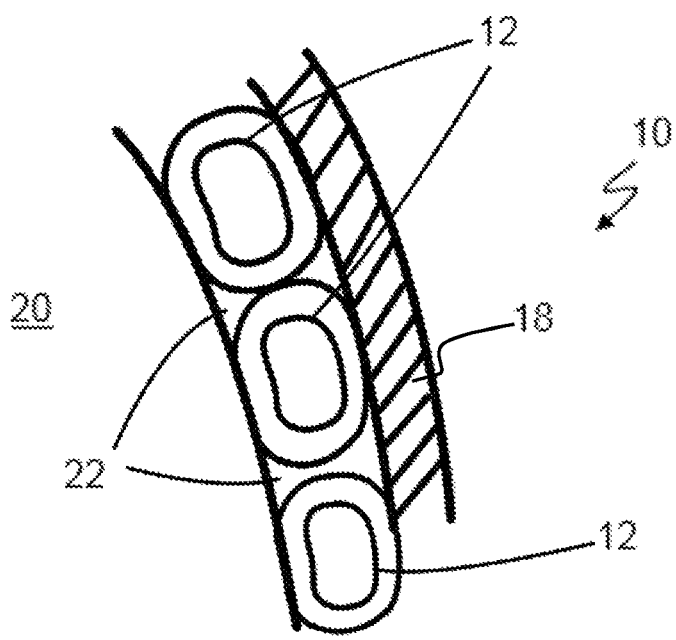
Figure 9:
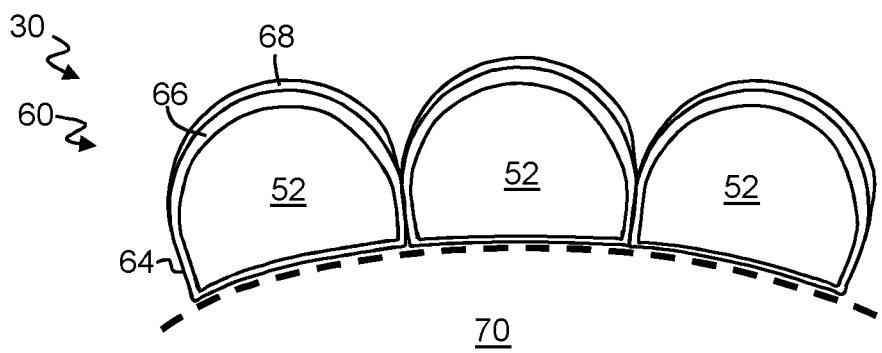
FIG. 9 shows the cross-sectional region presented in FIG. 8 in contact with a curved body.

FIG. 9 shows the layer 60 in contact with an object 70 in an operational state in which fluid is flowing through the passageway 52. The object 70 may be any object in need of temperature regulation, for example a human body part, which may be a head, or may be some other object. The object 70 has an uneven and arcuate profile but because of the nature of the material of which the first side 64 is comprised, the first side is deformable to substantially take up the shape of the outer surface of the object 70. Deformation occurs in part because the flexible material of the first side 64 will deform when pressed up against the object 70. Deformation also occurs because the fluid through the passageway 52 is under pressure and hence causes the first side 64 to "inflate" to press against the surface of the object 70. The second side 66 of the layer 60 is less flexible and hence will maintain its formed shape. Although there will be minor gaps between the walls of the first side 64 of adjacent passageway runs 52, these are minor in comparison to the configuration of the related art, as shown in FIGS. 2, 3. Hence, in operation, a heat exchanger of the present disclosure will conform to a larger percentage of the outer surface of an object 70, and hence provide a larger, or substantially "uninterrupted", interface surface over which heat may be exchanged between the fluid passing through the passage 52 and the surface of the object 70. Since the wall of the first side 64 is also specially configured to have a high thermal conductivity, the heat transfer will be further enhanced.

In examples where the fluid passing through the passages 62 is a coolant, the device of the present disclosure is advantageous of the over the related art, as the second side 66 of the layer 60 has an insulatory layer 68. Hence the fluid passing through the passageway 52 will be insulated from environmental heat, such that the only heat source which has access to the fluid in the passageway 52 is the object 70 itself, therefore improving the cooling efficiency per volumetric unit flow of the coolant.

Although the examples shown in FIGS. 4, 5, 6 are heat exchangers configured to be placed into contact with a human head, other examples of the heat exchanger of the present disclosure may be configured to be placed into contact with another part of the body, or another object, to regulate the control of temperature of the object.

Figure 10:
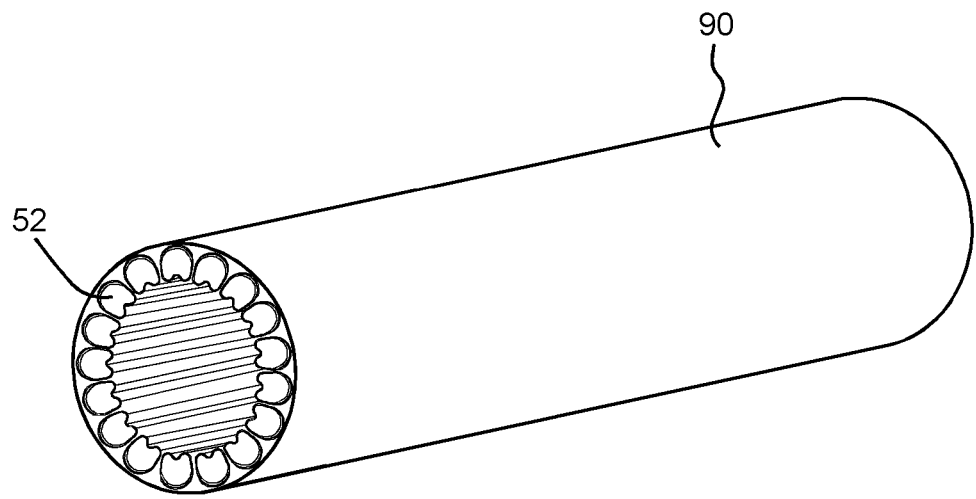
FIG. 10 shows an alternative configuration of heat exchanger according to the present disclosure.

As shown in FIG. 10, the heat exchanger may also be provided in the form of a tube or sleeve 90 where the passage 52 has a similar serpentine/boustrophedonic route from one end of the sleeve to the other. Hence in use, the object to be cooled is located within the hollow passage of the tube 90. Such applications might be cooling or maintaining temperature in a flow duct, or a human or animal body part.

Figure 11:
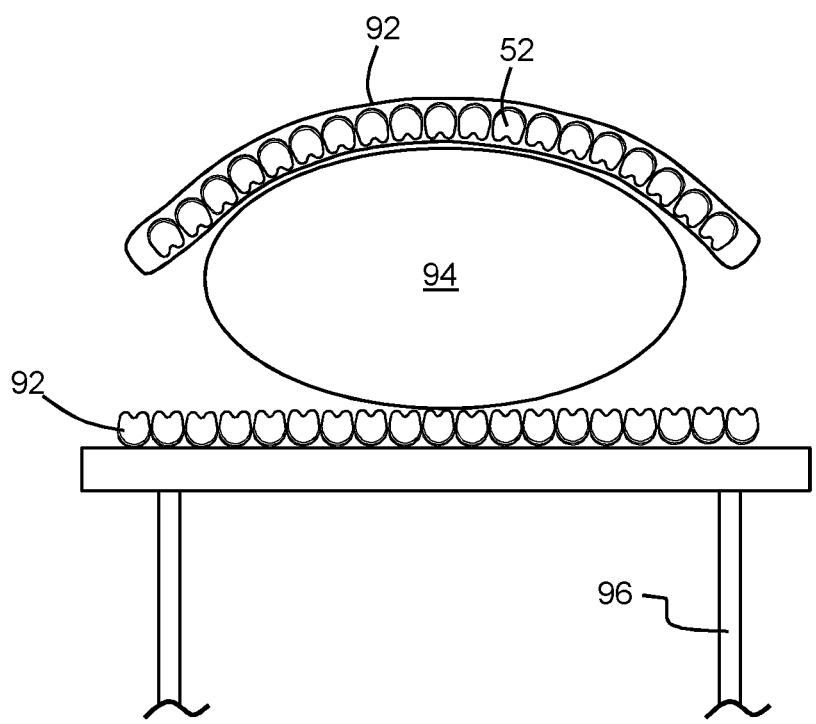
FIG. 11 shows a further alternative example of a heat exchanger according to the present disclosure.

Alternatively, as shown in FIG. 11, the heat exchanger of the present disclosure may also be provided as a sheet 92 for an object 94 to sit upon and/or to be covered by, as shown in FIG. 11. Likewise the passages 52, as the previous examples, may be provided in a boustrophedonic route along the lengths of the sheet 92. In the example shown, the object 94 may be the body of a human, which is undergoing a medical procedure requiring them to be kept at a regulated constant, elevated or reduced temperature. Hence the object 94 may be laid on a table 96 wrapped or covered in the heat exchanger 92.

In the examples of FIG. 10 and FIG. 11, the heat exchanger is connected to a temperature regulation system 34 as described with reference to FIG. 4. Hence each of the heat exchangers of FIGS. 10 and 11 will have an inlet and an outlet tube feeding to the temperature regulation system 34.

A method of manufacture the heat exchanger 30 will now be described with reference to FIGS. 12 to 15.

Figure 12:
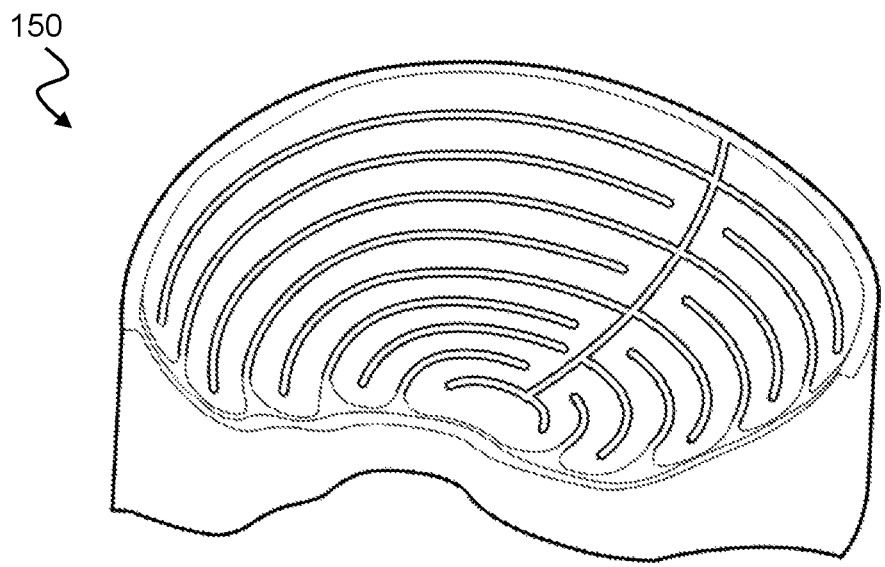
FIG. 12 shows a view of a former for a side section of the heat exchanger of the present disclosure.
Figure 13:
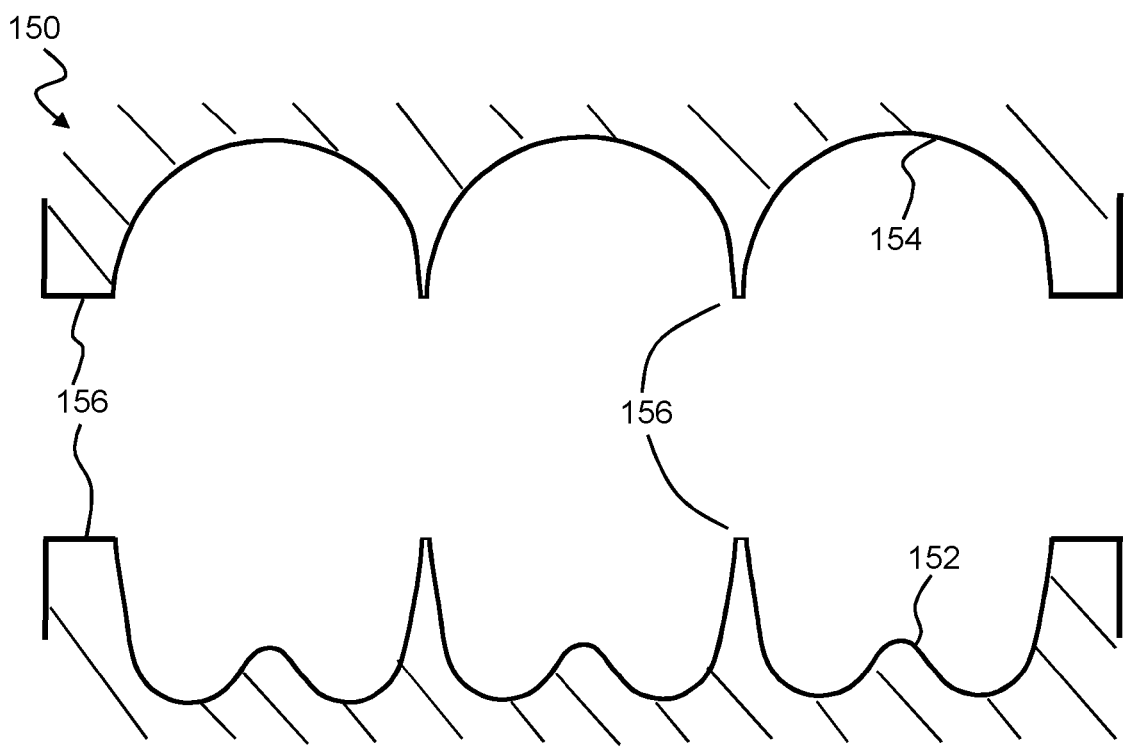
FIG. 13 shows two halves of a former for the manufacture of an element of the heat exchanger of the present disclosure.

FIG. 12 shows a side view of a former used to shape the side element of the heat exchanger 30 for use with a human head as shown in FIGS. 4, 5, 6. In this example it can be seen that the former comprises a single channel in a serpentine configuration to provide the route as described in relation to the heat exchanger layer 60. FIG. 13 shows two halves of a former assembly 150, or at least a region of a former assembly 150, comprising a first half 152 being formed to define the first side 64 of the material layer 60 of the heat exchanger, and a second half 154 being formed to define the second side 66 of the material layer 60. As can be seen from the cross-section in FIG. 13, the shape of the former is substantially identical to that of the walls which define the passage 52.

That is to say, the method of manufacture of the heat exchanger 30 comprises providing a first former element 152 which defines the external shape of one side of the layer 60, and providing a second former 154 having a surface which defines the external shape of the other side of the layer 60. The patterns of both formers are complementary in shape to thereby define the route of the passageway 52 and the layer 60.

Figure 14:
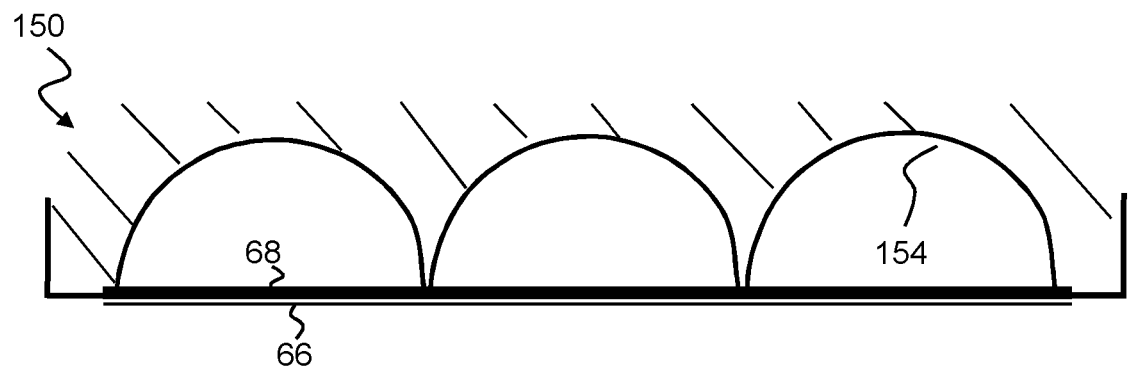
FIG. 14 shows the same view as FIG. 13 with the addition of pre-cursor layers of heat exchanger material provided in the former.
Figure 14:
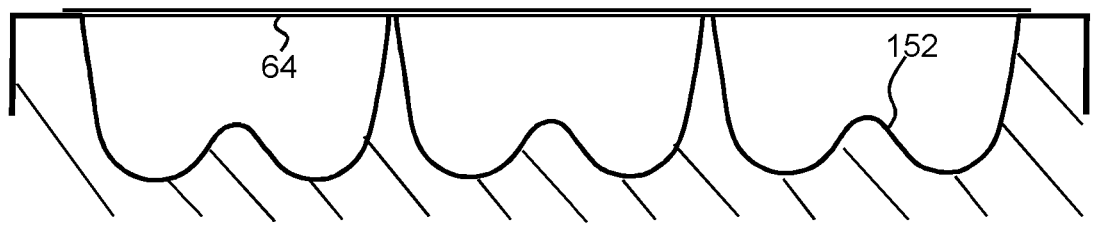

As shown in FIG. 14, the method further comprises the step of sandwiching a sheet of the first material 64 next to a sheet of the second material 66 such that the first sheet 64 separates the first former 152 from the second sheet 66, and the second sheet 66 separates the second former 154 from the first sheet 64.

Figure 15:
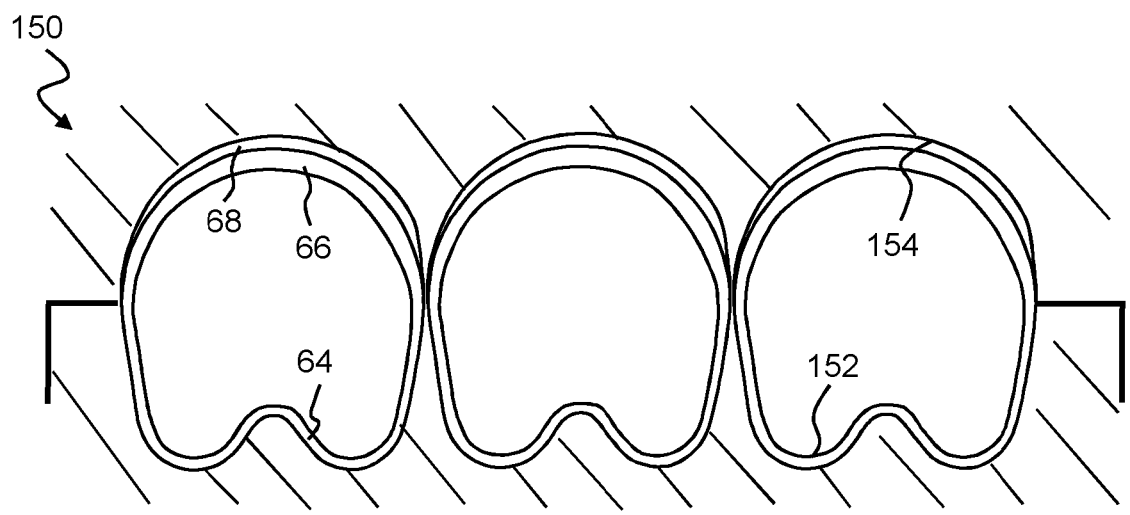
FIG. 15 shows the two halves of the former shown in FIG. 14 brought together to form a region of the heat exchanger.

As shown in FIG. 15, the method further comprises the step of executing a joining process including bringing the two formers 152, 154 together such that the first material sheet 64 and second material sheet 66 are brought into contact to undergo a joining process.

The joining process comprises bringing the material layers 64, 66 together at ambient conditions, that is to say in the absence of an elevated temperature. This can be achieved as the first sheet material 64 and second sheet material 66 comprise a silicone rubber having material properties which cause it to bond under the influence of pressure. Hence, it will only bond at the regions of the former which are in contact (namely shoulders 156 shown in FIG. 13), and not bond in the "open" regions which define the passageway 52.

When the formers 152, 154 are together, and the regions of the sheets 64,66 are bonded at shoulder regions 156, the internal passageways defined by the formers 152,154 are at least partially evacuated to thereby force (or "suck") the first and second sheet materials 64,66 towards the walls of the formers 152, 154, thereby deforming the sheet materials to the shape of the former and thereby provide the sheets with the desired external cross-sectional shape to produce the layer 60 having a passageway 52.

As previously described, the former may define the shape of at least part of a cap to conform for a human or animal head, or of sections of a cap to be joined to other sections to make a cap.

The insulatory layer 68 may be included with the sheet material layer 66 in the forming process, or added later as a separate manufacturing step.

Other layers may be added on the external surface of the layer 60. A liner may also be provided on the first side of the layer which in use would be provided between the object and the material layer 60.

Although in the examples above, the layer 60 is described as being silicone rubber based, other materials may be used in addition or as an alternative to silicone rubber. Likewise, methods of bonding the layers 64,66 together other than one described above may be used, for example thermal bonding and/or use of an adhesive.

There is thus provided a heat exchanger and a method of manufacture of a heat exchanger which provide a significant advantage over that of the related art. Not only does the heat exchanger itself improve contact with an object to be temperature controlled by virtue of the geometry and material choice of the layer 60, the method of manufacture of the heat exchanger is an improvement of the manufacture of equivalent known heat exchangers in that it is more repeatable and faster to create each device.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A heat exchanger cap configured for wearing on a human head, the heat exchanger cap comprising:
   a layer of material defining a passageway through which a heat transfer fluid may flow, the material layer defining
      a first element positioned to cover a first lateral side of the head;
      a second element positioned to cover an opposing second lateral side of the head;
      an intermediate joining element that is joined to and spaces apart the first and second elements, the intermediate joining element positioned to cover a medial section of the head and positioned to extend between a nominal front to a nominal back of the cap;
   each of the first, second, and joining elements defining a section of the passageway through the cap to move the heat transfer fluid;
   the material layer having:
      a first side for contact with the head; and
      a second side which, in use, will face away from the head;
   the first side has a relatively high coefficient of thermal conduction;
   the second side has a relatively low coefficient of thermal conduction compared to the first side;
   the passageway extending from a single inlet to a single outlet;
   in at least the first element and the second element, the single passageway defines flow regions on both sides of a junction line with the flow regions located on opposing sides of the junction line and with a first one of the flow regions positioned to cover an anterior section of the head and a second one of the flow regions positioned to cover a posterior section of the head.

2. The heat exchanger as claimed in claim 1, wherein the first side is relatively flexible and configured to be compliant and to conform to the shape of the surface of the head and the second side is relatively inflexible compared to the first side.

3. The heat exchanger as claimed in claim 1, wherein the first side comprises a relatively thin silicone based wall, and the second side comprises a relatively thick silicone based wall compared to the first side.

4. The heat exchanger as claimed in claim 3, wherein the wall of the first side comprises aluminium particles.

5. The heat exchanger as claimed in claim 3, wherein the second side comprises an insulatory layer outward of both of the silicone based walls.

6. The heat exchanger as claimed in claim 1, wherein at least part of the first side has, in a non-deformed state, a double arced outer surface with both arcs configured for contact with the head.

7. The heat exchanger as claimed in claim 1, wherein at least part of the second side has, in a non-deformed state, a single arcuate outer surface.

8. A cap to be worn on a human or animal head, the cap comprising:
   a layer of material defining a passageway through which a heat transfer fluid may flow, the material layer defining:
      first and second elements configured to respectively cover different lateral sections of the head;
      an intermediate joining element that is joined to and spaces apart the first and second elements, the joining element configured to be aligned in a sagittal plane;
   each of the elements defining a section of the passageway through which the heat transfer fluid flows;
   the material layer having:
      a first side for contact with the head; and
      a second side which, in use, will face away from the head;
   the first side has a relatively high coefficient of thermal conduction;
   the second side has a relatively low coefficient of thermal conduction compared to the first side;
   the passageway has a boustrophedonic route throughout the majority of the layer, the passageway extending from a single inlet to a single outlet;
   in the first element and the second element, the single passageway defines flow regions on both sides of a junction line with each of the flow regions extending only part of the way from the nominal front to the nominal back of the cap, with the flow regions located on opposing sides of the junction line that is configured to be aligned in a coronal plane, the passageway in each of the flow regions of the first and second elements comprising a boustrophedonic route aligned in a direction from back to front of the element, the junction line dividing each of the first and second elements into anterior and posterior sections;
   the material layer comprises adjacent runs of the passageway next to one another such that, in use, the first side of the material layer provides a substantially uninterrupted interface surface with the surface of the head.

9. A method of manufacturing a heat exchanger cap that comprises a layer of material defining a passageway through which a heat transfer fluid may flow with the material layer having a first side for contact with a human head and a second side which, in use, will face away from the human head, the method comprising:
   providing a first former having a surface pattern which defines the external shape of one side of the layer;
   providing a second former having a surface pattern which defines the external shape of the other side of the layer;
   the patterns of both formers being complementary in shape to thereby define the route of the passageway in the layer and defining a first element configured to cover a first lateral side of the head, a second element configured to cover a second lateral side of the head, and an intermediate joining element configured to cover a medial section of the head and that spaces apart the first and second elements, in at least the first element and the second element, the passageway defines flow regions on both sides of a junction line that is configured to be positioned in a coronal plane with each of the flow regions extending only part of the way, and not the whole of the way, from a nominal front to a nominal back of the cap, with the flow regions located on opposing sides of the junction line and with the passageway in each of the flow regions of the first and second elements comprising a boustrophedonic route aligned in a direction from back to front of the element;
   sandwiching a sheet of the first material next to a sheet of the second material such that the first sheet separates the first former from the second sheet, and the second sheet separated the second former from the first sheet; and
   executing a joining process including bringing the first and second formers together such that the first material sheet and second material sheet are brought into contact to undergo a joining process with the first side having a relatively high coefficient of thermal conduction and the second side having a relatively low coefficient of thermal conduction compared to the first side.

10. The method as claimed in claim 9, wherein the joining process comprises bringing the layers together at ambient temperature conditions.

11. The method as claimed in claim 9, wherein the first sheet material and second sheet material comprise a silicone rubber.

12. The method as claimed in claim 9, further comprising:
when the formers are together, at least partially evacuating the internal passageways of the former thereby forcing the first and second sheet materials towards the walls of the formers, thereby deforming the sheet materials to the shape of the former to thereby provide the sheet with a desired external cross sectional shape.

* * * * *